United States Patent
Miller et al.

(10) Patent No.: US 9,060,938 B2
(45) Date of Patent: *Jun. 23, 2015

(54) PHARMACEUTICAL COMPOSITIONS OF ACTIVE AGENTS AND CATIONIC DEXTRAN POLYMER DERIVATIVES

(75) Inventors: Warren K. Miller, Bend, OR (US);
Michael M. Morgen, Bend, OR (US);
Corey J. Bloom, Bend, OR (US)

(73) Assignee: Bend Research, Inc., Bend, OR (US)

( * ) Notice: Subject to any disclaimer, the term of this patent is extended or adjusted under 35 U.S.C. 154(b) by 428 days.

This patent is subject to a terminal disclaimer.

(21) Appl. No.: 13/468,997

(22) Filed: May 10, 2012

(65) Prior Publication Data

US 2012/0288491 A1    Nov. 15, 2012

Related U.S. Application Data

(60) Provisional application No. 61/484,552, filed on May 10, 2011.

(51) Int. Cl.
| | |
|---|---|
| A61K 31/721 | (2006.01) |
| A61K 9/14 | (2006.01) |
| A61K 9/72 | (2006.01) |
| A61K 9/16 | (2006.01) |
| A61K 9/00 | (2006.01) |
| A61K 31/4422 | (2006.01) |
| C08B 37/02 | (2006.01) |
| C08L 5/02 | (2006.01) |

(52) U.S. Cl.
CPC ............. *A61K 9/1652* (2013.01); *A61K 9/0075* (2013.01); *A61K 31/4422* (2013.01); *C08B 37/0021* (2013.01); *C08L 5/02* (2013.01)

(58) Field of Classification Search
CPC . A61K 9/0012; A61K 9/0014; A61K 9/0019; A61K 9/0031; A61K 9/0034; A61K 9/14; A61K 9/0048; A61K 9/0051; A61K 9/0053; A61K 9/006; A61K 9/007; A61K 9/0075; A61K 38/02; A61K 47/36
USPC ........ 424/499, 130.1, 184.1; 514/1.1, 43, 777
See application file for complete search history.

(56) References Cited

U.S. PATENT DOCUMENTS

| | | | |
|---|---|---|---|
| 4,451,452 A | 5/1984 | Deibig et al. | |
| 4,501,726 A | 2/1985 | Schroder et al. | |
| 4,615,881 A | 10/1986 | Deibig et al. | |
| 5,688,931 A | 11/1997 | Nogusa et al. | |
| 6,048,515 A | 4/2000 | Kresse et al. | |
| 6,541,039 B1 | 4/2003 | Lesniak et al. | |
| 6,576,221 B1 | 6/2003 | Kresse et al. | |
| 6,589,562 B1 | 7/2003 | Shefer et al. | |
| 2002/0076443 A1 | 6/2002 | Stein et al. | |
| 2004/0176391 A1 | 9/2004 | Weers et al. | |
| 2005/0058710 A1 | 3/2005 | Straub et al. | |
| 2006/0204582 A1 | 9/2006 | Stein et al. | |
| 2007/0065373 A1 | 3/2007 | Morton et al. | |
| 2008/0234227 A1 | 9/2008 | Soula et al. | |
| 2008/0241267 A1 | 10/2008 | Verrijk | |
| 2012/0003282 A1 | 1/2012 | Miller et al. | |
| 2012/0058196 A1 | 3/2012 | Friesen et al. | |

FOREIGN PATENT DOCUMENTS

| | | |
|---|---|---|
| DE | 4136324 | 5/1993 |
| DE | 4208946 | 9/1993 |
| EP | 0053580 | 6/1982 |
| WO | WO 02/083154 | 10/2002 |
| WO | WO 2008/038111 | 4/2008 |
| WO | WO 2008/070538 | 6/2008 |
| WO | WO 2008/151022 | 12/2008 |
| WO | WO 2010/102065 | 9/2010 |
| WO | WO 2010/102066 | 9/2010 |
| WO | WO 2010/132827 | 11/2010 |
| WO | WO 2011/057017 | 5/2011 |
| WO | WO 2011/060250 | 5/2011 |

OTHER PUBLICATIONS

Cruz, et al., "Peptide Synthesis Containing a B-Cell and a T-Cell Epitope on Dextran Beads and Evaluation of Humoral Response Against Bead-Peptide Construct," *Letters in Peptide Science*, 7: 229-237, 2000.
Heinze et al., "Functional Polymers Based on Dextran," *Advances in Polymer Science*, vol. 205, pp. 199-291 (Sep. 2006).
International Search Report and Written Opinion, dated Feb. 22, 2011, issued in corresponding International Application No. PCT/2010/056515.
Liebert et al., "Nanoparticles on the Basis of Highly Functionalized Dextrans," *Journal of the American Chemical Society*, vol. 127, No. 30, pp. 10484-10485 (Aug. 2005).
Prado et al., "Preparation and characterization of a novel starch-based interpolyelectrolyte complex as matrix for controlled drug release," *Carbohydrate Research*, vol. 344, No. 11, pp. 1325-1331 (Jul. 2009).

*Primary Examiner* — Richard Schnizer
*Assistant Examiner* — Alma Pipic
(74) *Attorney, Agent, or Firm* — Klarquist Sparkman, LLP (57) ABSTRACT

Solid dry powder compositions comprising active agents and dextran polymer derivatives comprising an ester-linked amine-containing substituent and an alkyl ester substituent are disclosed, as are methods for making such compositions.

20 Claims, 4 Drawing Sheets

FIG. 4

PHARMACEUTICAL COMPOSITIONS OF ACTIVE AGENTS AND CATIONIC DEXTRAN POLYMER DERIVATIVES

CROSS REFERENCE TO RELATED APPLICATION

This application claims priority to and the benefit of U.S. Provisional Patent Application No. 61/484,552, filed on May 10, 2011, which is incorporated herein in its entirety by reference.

TECHNICAL FIELD

Solid dry powder compositions comprising active agents and cationic dextran polymer derivatives comprising an ester-linked amine-containing substituent and an alkyl ester substituent are disclosed.

BACKGROUND

Pharmaceutically active agents are generally formulated as solid or liquid dosage forms for administration. Such dosage forms generally comprise the active agent combined with excipients to form materials that may be conveniently and reliably administered to a patient in need of such therapy, and following administration, the active agent is absorbed and distributed in the patient in a way that leads to good efficacy and safety.

Cationic polymers have previously been used for extended or controlled release of active agents near the site of delivery. Some cationic polymers have been evaluated for this purpose and in some cases have been referred to as "mucoadhesive." Examples of cationic mucoadhesive excipients include chitin, chitosan, and amino-substituted polyacrylates and polymethacrylates.

SUMMARY

Embodiments of a cationic dextran derivative suitable for use in a wide variety of formulations are disclosed. Methods of making and using the cationic dextran derivatives also are disclosed.

Embodiments of a solid dry powder composition comprising an active agent and a cationic dextran polymer derivate are disclosed. The cationic dextran polymer derivative comprises (i) an ester-linked amine-containing substituent, selected from and mixtures thereof, wherein $R_1$ is selected from $C_1$, $C_2$, $C_3$, or $C_4$ alkyl groups, $R_2$ and $R_3$ may be the same or different and are selected from hydrogen, methyl and ethyl groups, and $R_4$, $R_5$, and $R_6$ may be the same or different and are selected from methyl and ethyl groups, and wherein the degree of substitution of said ester-linked amine-containing substituent is at least 0.03; and (ii) an alkyl ester substituent selected from acetate, propionate, butyrate, isobutyrate, and mixtures thereof, wherein the degree of substitution of said alkyl ester substituent is at least 0.05.

In one embodiment, the ester-linked amine-containing substituent is wherein $R_1$ is selected from $C_1$, $C_2$, $C_3$, or $C_4$ alkyl groups, and $R_2$ and $R_3$ may be the same or different and are selected from hydrogen, methyl and ethyl groups. In one embodiment, $R_1$ is a $C_2$ alkyl group, and $R_2$ and $R_3$ are hydrogens.

In another embodiment, the ester-linked amine-containing substituent is wherein $R_1$ is selected from $C_1$, $C_2$, $C_3$, or $C_4$ alkyl groups, and $R_4$, $R_5$, and $R_6$ may be the same or different and are selected from methyl and ethyl groups. In one embodiment, $R_1$ is a $C_3$ alkyl group, and $R_4$, $R_5$, and $R_6$ are methyl groups.

In one embodiment, the ester-linked amine-containing substituent has a degree of substitution of at least 0.05. In still another embodiment, the ester-linked amine-containing substituent has a degree of substitution of at least 0.1.

In another embodiment, the degree of substitution of the alkyl ester substituent is at least 0.1. In another embodiment, the degree of substitution of the alkyl ester substituent is at least 0.5. In still another embodiment, the degree of substitution of the alkyl ester substituent is at least 1.0.

The cationic dextran polymer derivatives disclosed herein have unique properties that make them suitable for a wide variety of applications.

By combining an ester-linked amine-containing substituent with an alkyl ester substituent, compositions containing the cationic dextran derivative can associate with anionic active agents, other anionic formulation materials, and anionic endogenous materials. Such materials can, among other uses, help retain active agents near the site of delivery and action. Specifically, the cationic groups of the cationic dextran polymer derivative can associate with anionic groups on anionic materials such as proteins, peptides, and oligonucleotides. However, the addition of the alkyl ester groups reduces the water solubility of the cationic dextran and promotes association with the anionic materials. Such association can, in some cases, form complexes, aggregates, nanoparticles, or precipitates.

In addition, the combination of an ester-linked amine-containing substituent with an alkyl ester substituent provides tunability and flexibility to the researcher to achieve a polymer with the properties that are ideal for the specific therapeutic target. By adjusting the ratio of the ester-linked amine-containing substituent to the alkyl ester substituent, factors such as aqueous solubility, dissociation constant (pKa), mucoadhesion, and/or solubility in organic solvents can be optimized for the required task.

Unlike other cationic polymers, such as amine-functionalized acrylates or methacrylates (for example, some grades of excipients sold under the name EUDRAGIT®), certain embodiments of the cationic dextran polymer derivatives are biocompatible and biodegradable, and therefore are more suitable for parenteral administration.

In some embodiments, the composition is formulated for administration to a human or animal via a mode selected from oral, buccal, mucosal, sublingual, intravenous, intra-arterial, intramuscular, subcutaneous, intraperitoneal, intraarticular, infusion, intrathecal, intraurethral, topical, subdermal, transdermal, intranasal, inhalation, pulmonary tract, intratracheal, intraocular, ocular, intraaural, vaginal, and rectal. In certain embodiments, the composition is formulated for administration to a human or animal via inhalation. In one embodiment, the composition is formulated for delivery to the upper airways. In another embodiment, the composition is formulated for delivery to the lower airways. In yet another embodiment, the composition is formulated for delivery to the nasal passages.

In one embodiment, the solid dry powder composition comprises an active agent selected from a small molecule, a biological active agent, and mixtures thereof.

In another embodiment, the active agent is a biological active agent selected from proteins, antibodies, antibody fragments, antigens, peptides, oligonucleotides, vaccines, and mixtures and derivatives thereof.

In one embodiment, a method includes providing an embodiment of the solid dry powder composition formulated for inhalation by a human or animal. In one embodiment, the composition is formulated for delivery to the upper airways. In another embodiment, the composition is formulated for delivery to the lower airways. In yet another embodiment, the composition is formulated for delivery to the nasal passages.

DETAILED DESCRIPTION OF PREFERRED EMBODIMENTS

The present disclosure relates to solid dry powder compositions comprising active agents and cationic dextran polymer derivatives comprising an ester-linked amine-containing substituent and an alkyl ester substituent. Embodiments of cationic dextran polymer derivatives and methods for making them are described in detail below.

Unless otherwise indicated, all numbers expressing quantities of ingredients, properties such as molecular weight, percentages, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Active Agents

In one embodiment, the compositions of the invention are suitable for use with any biologically active compound desired to be administered to a patient in need of the active agent. The compositions may contain one or more active agents. As used herein, by "active agent" is meant a drug, medicament, pharmaceutical, therapeutic agent, nutraceutical, or other compound that may be desired to be administered to the body. The active agent may be a "small molecule," generally having a molecular weight of 2000 Daltons or less. The active agent may also be a "biological active agent." Biological active agents include proteins, antibodies, antibody fragments, antigens, peptides, oligonucleotides, vaccines, and various derivatives of such materials. In one embodiment, the active agent is a biological active agent selected from proteins, antibodies, antibody fragments, antigens, peptides, oligonucleotides, vaccines, and mixtures and derivatives thereof. In one embodiment, the active agent is a small molecule. In another embodiment, the active agent is a biological active agent. In one embodiment, the active agent is selected from a small molecule, a biological active agent, and mixtures thereof. In still another embodiment, the active agent is a mixture of a small molecule and a biological active agent.

The active agent may be highly water soluble (i.e., greater than 100 mg/mL at 25° C.), sparingly water soluble (i.e., 5-30 mg/mL), or poorly water soluble (i.e., less than 5 mg/mL). In one embodiment, the active agent is "poorly water soluble," and the active agent has a solubility in water (at 25° C.) of less than 5 mg/mL. The active agent may have an even lower water solubility, such as less than 1 mg/mL, less than 0.1 mg/mL, and even less than 0.01 mg/mL.

The active agent should be understood to include the non-ionized form of the active agent, pharmaceutically acceptable salts of the active agent, or any other pharmaceutically acceptable forms of the active agent. By "pharmaceutically acceptable forms" is meant any pharmaceutically acceptable derivative or variation, including stereoisomers, stereoisomer mixtures, enantiomers, solvates, hydrates, isomorphs, polymorphs, pseudomorphs, neutral forms, salt forms and prodrugs.

Examples of classes of active agents include, but are not limited to, compounds for use in the following therapeutic areas: antihypertensives, antianxiety agents, antiarrythmia agents, anticlotting agents, anticonvulsants, blood glucose-lowering agents, decongestants, antihistamines, antitussives, antineoplastics, beta blockers, anti-inflammatories, antipsychotic agents, cognitive enhancers, anti-atherosclerotic agents, cholesterol-reducing agents, triglyceride-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-angiogenesis agents, anti-glaucoma agents, anti-depressants, bronchodilators, glucocorticoids, steroids, and antiviral agents.

Cationic Dextran Polymer Derivatives

Cationic dextran polymer derivatives are polymers formed by the derivatization of dextran with ester-linked groups. Dextran is an α-D-1,6-glucose-linked glucan. It may have side-chains linked to the backbone of the dextran polymer, with the degree of branching approximately 5%, and the branches are mostly 1-2 glucose units long. A representative structure of the repeat unit of dextran is illustrated below.

In one embodiment, the dextran used to form the cationic dextran polymer derivative has a molecular weight that may range from 1,000 to 200,000 daltons. As used herein, by "molecular weight" is meant the number-average molecular weight as determined by chromatographic methods well known in the art. In these methods, the number-average molecular weight corresponds to the arithmetic mean of the molecular weights of individual macromolecules. In another embodiment, the dextran used to form the cationic dextran polymer derivative has a molecular weight of from 1,000 to 70,000 daltons. In still another embodiment, the dextran used to form the cationic dextran polymer derivative has a molecular weight of from 1,000 to 20,000 daltons. The resulting cationic dextran polymer derivative may have a molecular weight ranging from 1,400 to 200,000 daltons, from 1,400 to 70,000 daltons, or even from 1,400 to 25,000 daltons.

Embodiments of the cationic dextran polymer derivatives as used herein comprise an ester-linked amine-containing substituent. The ester-linked amine-containing substituent is selected from and mixtures thereof, wherein $R_1$ is selected from $C_1$, $C_2$, $C_3$, or $C_4$ alkyl groups, $R_2$ and $R_3$ may be the same or different and are selected from hydrogen, methyl and ethyl groups, and $R_4$, $R_5$, and $R_6$ may be the same or different and are selected from methyl and ethyl groups.

In one embodiment, the ester-linked amine-containing substituent is wherein $R_1$ is selected from $C_1$, $C_2$, $C_3$, or $C_4$ alkyl groups, and $R_2$ and $R_3$ may be the same or different and are selected from hydrogen, methyl and ethyl groups. It is to be understood that while the above ester-linked amine-containing substituent is shown to be in a non-ionized form, the above substituent is meant to include any ionized forms and salt forms, as one skilled in the art would understand. In another embodiment $R_1$ is a $C_2$ alkyl group, and $R_2$ and $R_3$ are hydrogens.

In another embodiment, the ester-linked amine-containing substituent is wherein $R_1$ is selected from $C_1$, $C_2$, $C_3$, or $C_4$ alkyl groups, and $R_4$, $R_5$, and $R_6$ may be the same or different and are selected from methyl and ethyl groups. In one embodiment, $R_1$ is a $C_3$ alkyl group, and $R_4$, $R_5$, and $R_6$ are methyl groups.

In one embodiment, the ester-linked amine-containing substituent is characterized by a dissociation constant, known as the pKa. If the pH of a solution containing the ester-linked amine-containing substituent is the same as the pKa value, then 50 mol % of the ester-linked amine-containing substituents are ionized, and 50 mol % are non-ionized. As the pH decreases, a greater fraction of the ester-linked amine-containing substituents become ionized; as the pH increases, a greater fraction of the ester-linked amine-containing substituents become non-ionized.

The degree of substitution of the ester-linked amine-containing substituent is at least 0.03. As used herein, the term "degree of substitution" refers to the average number of substituents attached to one repeat, or monomer, of the dextran backbone; the maximum number of ester-linked amine-containing substituents that can be attached to a dextran backbone monomer is 3.0. In another embodiment, the degree of substitution of the ester-linked amine-containing substituents is at least 0.05. In other embodiments, higher degrees of substitution are desired. Thus, the degree of substitution of the ester-linked amine-containing substituents may be at least 0.10, at least 0.15, at least 0.2, or even higher.

In another embodiment, the degree of substitution of the ester-linked amine-containing substituents ranges from 0.03 to 2.95. In yet another embodiment, the degree of substitution of the ester-linked amine-containing substituents ranges from 0.05 to 2.95. Other degrees of substitution of the ester-linked amine-containing substituents may be beneficial, including from 0.05 to 2.95, from 0.1 to 2.5, from 0.15 to 2.0, and even from 0.2 to 2.0.

The cationic dextran polymer derivative further comprises an alkyl ester substituent selected from acetate, propionate, butyrate, isobutyrate, and mixtures thereof. In another embodiment, the alkyl ester substituent is selected from acetate and propionate. In yet another embodiment, the alkyl ester substituent is acetate. In another embodiment, the alkyl ester substituent is propionate.

The degree of substitution of the alkyl ester substituent is at least 0.05. In another embodiment, the degree of substitution of the alkyl ester substituent is at least 0.1. In still another embodiment, the degree of substitution of the alkyl ester substituent is at least 0.5. In yet another embodiment, the degree of substitution of the alkyl ester substituent is at least 1.0. In another embodiment, the degree of substitution of the alkyl ester substituent ranges from 0.05 to 2.95. In another embodiment, the degree of substitution of the alkyl ester substituent ranges from 0.1 to 2.5.

The degree of substitution of the substituents may be chosen such that the polymer has the desired physical properties. In one embodiment, the degree of substitution is adjusted to obtain a cationic dextran polymer derivative with the desired aqueous solubility or dispersability. A test to determine the aqueous solubility of a cationic dextran polymer derivative may be performed as follows. The cationic dextran polymer derivative is initially present in bulk powder form with an average particle size of greater than 1 micron. The polymer alone is administered at a concentration of 0.2 mg/mL to a buffer solution at the desired pH and stirred for approximately 1 hour at room temperature. Next, a nylon 0.45 µm filter is weighed, and the solution is filtered. The filter is then dried overnight at 40° C., and weighed the next day. The aqueous solubility of the polymer is calculated from the amount of polymer added to the buffer solution minus the amount of polymer remaining on the filter.

Similar procedures can be used to determine the effect of pH on the aqueous solubility of the cationic dextran polymer derivatives. In this case the procedures are performed using aqueous buffer solutions with various pH values.

As used herein, by "aqueous soluble" is meant that the cationic dextran polymer derivative has an aqueous solubility of at least 1 mg/mL in a given aqueous solution over the pH range and temperature specified for the aqueous solution. By "poorly aqueous soluble" is meant that the polymer has a solubility of less than 0.1 mg/mL in a given aqueous solution over the pH range and temperature specified for the aqueous solution. Factors affecting the aqueous solubility of the cationic dextran polymer derivative include the alkyl ester substituent and its degree of substitution, the ester-linked amine-containing substituent and its degree of substitution, the pKa of the ester-linked amine-containing substituent, the ratio of the degree of substitution of the alkyl ester substituent to the degree of substitution of the ester-linked amine-containing substituent, the pH of the aqueous solution, and/or the temperature of the aqueous solution.

In one embodiment, the cationic dextran polymer derivative is poorly aqueous soluble at a pH that is equal to or greater than the pKa value of the ester-linked amine-containing substituent, but aqueous soluble at a pH less than the pKa value minus 1.

In another embodiment, the degree of substitution of the alkyl ester substituent is sufficiently high such that when the ester-linked amine-containing substituent is non-ionized or substantially non-ionized, the cationic dextran polymer derivative is poorly aqueous soluble.

In another embodiment, the cationic dextran polymer derivative is biocompatible. By "biocompatible" is meant that for one or more delivery routes, the polymer is compatible with and has no significant toxic effect on the living organism to which it is administered. In one embodiment, the polymer does not significantly elicit humoral or cell-based immune responses when administered in vivo.

In yet another embodiment, the cationic dextran polymer derivative is biodegradable. By "biodegradable" is meant that the polymer will degrade when administered in vivo. By "degrade" is meant that in an in vivo use environment, the polymer is broken down into smaller species that can be absorbed, metabolized, and/or otherwise eliminated or "cleared" from the use environment within a time period of several days to several weeks or even several months. This degradation can occur through enzymatic, hydrolytic, oxidative, or other reactions or processes, as are well known in the art. The polymer may also degrade into aqueous soluble species that can be cleared from the in vivo use environment. For example, the degradation products may be renally cleared through the kidneys or may enter the lymphatic system and then exit through the gastro-intestinal tract.

Synthesis of Cationic Dextran Polymer Derivatives

Cationic dextran polymer derivatives may be synthesized using procedures known in the art. In one embodiment, the ester-linked amine-containing substituent is first attached to the dextran polymer, and then the alkyl ester substituent is attached. In another embodiment, the alkyl ester substituent is first attached to the dextran polymer and then the ester-linked amine-containing substituent is attached to the dextran polymer. In still another embodiment, the ester-linked amine-containing substituent and the alkyl ester substituent are simultaneously attached to the dextran polymer.

In one embodiment, the cationic dextran polymer derivatives are synthesized using a homogeneous reaction by first dissolving the dextran polymer in a suitable solvent. Suitable solvents include, but are not limited to, dimethylformamide (DMF), dimethylacetamide (DMAC), formamide, dimethylsulfoxide (DMSO), methylene chloride, and mixtures thereof. Reactants and any catalysts and/or co-reactants are added to the reaction mixture, and the mixture is allowed to react at an appropriate temperature and for an appropriate time to achieve the desired degree of substitution. The reaction mixture may then be quenched, and the derivatized polymer precipitated and washed. The derivatized polymer may be purified prior to use or prior to further reaction. One skilled in the art will understand that standard polymer derivatization techniques may be applied to the synthesis of cationic dextran polymer derivatives. See for example *Advances in Polymer Science,* 205, *Polysaccharides II,* edited by Dieter Klemm (Springer-Verlag, Berlin Heidelberg, 2006). The specific reaction conditions used to attach the ester-linked amine-containing substituents and alkyl ester substituents will vary depending on the properties of the substituent. In addition, for some reactants, protecting groups may be added to the reactants, and after performing the reaction, the protecting groups may be removed to form the desired substituent.

When amine-containing substituents are ester linked to dextran, activation of the carboxylic acid and/or the use of coupling agents may be utilized to increase the rate of reaction and improve yield. Activation or coupling agents such as N,N'-carbonyldiimidazole (CDI) and N,N'-dicyclohexylcarbodiimide (DCC) may be employed. Similar reactions can be obtained using amine-containing substituents based on carboxylic acid chlorides and anhydrides. In some instances, a base may be used to catalyze the reaction. See for example, T. Heinze, et al., *Advances in Polymer Science,* Vol. 205, pp. 199-291, 2006. A similar reaction scheme can be used to attach alkyl ester substituents to the dextran polymer.

Dry Powder Compositions

In certain embodiments, the disclosed compositions are in the form of a solid dry powder comprising a plurality of particles. As used herein, the term "particles" means small pieces of matter having characteristic diameters of less than 3000 μm. In another embodiment, the particles are granulated into granules using standard methods known in the art, such as dry granulation, wet granulation, high shear granulation, and the like.

In one embodiment, the mean size of the particles is less than 500 μm. In another embodiment, the mean size of the particles is less than 200 μm. In still another embodiment, the mean size of the particles is less than 100 μm. In one embodiment, the mean size of the particles ranges from 0.5 to 500 μm. In another embodiment, the mean size of the particles ranges from 0.5 to 200 μm. In one embodiment, the mean size of the particles ranges from 0.5 to 100 μm. In one embodiment, the mean size of the particles ranges from 10 to 100 μm. In one embodiment, the mean size of the particles ranges from 10 to 70 μm. In one embodiment, the mean size of the particles ranges from 10 to 50 μm. In one embodiment, the mean size of the particles ranges from 0.5 to 10 μm. In one embodiment, the mean size of the particles ranges from 0.5 to 7 μm.

The active agent and cationic dextran polymer derivatives are collectively present in the particles in an amount ranging from 0.1 wt % to 100 wt %. In one embodiment, the active agent and cationic dextran polymer derivative constitute at least 5 wt % of the particles, at least 10 wt % of the particles, at least 25 wt % of the particles, at least 50 wt % of the particles, at least 75 wt % of the particles. In one embodiment, the particles consist essentially of the active agent and the cationic dextran polymer derivative. Materials may also be added to modify the charge, hydrophobicity, and/or dissolution rate of the composition.

In one embodiment, the active agent and cationic dextran polymer derivatives are collectively present in a plurality of the particles in an amount that is at least 1 wt %. In another embodiment, the active agent and cationic dextran polymer derivatives are collectively present in a plurality of the particles in an amount that is at least 10 wt %. In still another embodiment, the active agent and cationic dextran polymer derivatives are collectively present in a plurality of the particles in an amount that is at least 50 wt %.

The compositions comprising an active agent and cationic dextran polymer derivatives, may be formed by any method known in the art, including milling, extrusion, precipitation, or solvent addition followed by solvent removal. For example, the active agent and cationic dextran polymer derivatives may be processed by heat, mechanical mixing and extrusion using, for example, a twin-screw extruder. The product may then be milled to the desired particle size. In another example, the active agent and cationic dextran polymer derivatives are mixed with a solvent to form a liquid solution or liquid suspension. The compositions may then be formed from the liquid solution or suspension by any known process, including precipitation in a miscible non-solvent, emulsifying in an immiscible non-solvent, or by forming droplets followed by removal of the solvent by evaporation to produce particles.

In one embodiment, the particles are formed by spray drying. The active agent, cationic dextran polymer derivatives, and optional excipients may be added to a solvent. Thus, the fluid that is spray dried may be a suspension or a homogeneous solution or a combination of dissolved and suspended materials. In one embodiment, the fluid that is spray dried comprises a homogeneous solution of active agent and cationic dextran polymer derivatives dissolved together in a solvent. In another embodiment, the fluid that is spray dried consists essentially of a solution of active agent and cationic dextran polymer derivatives dissolved in a solvent.

The solvent may be any pharmaceutically acceptable solvent or mixture of solvents having a boiling point of less than 150° C. Suitable solvents include water, acetone, methanol, ethanol, methyl acetate, ethyl acetate, tetrahydrofuran (THF), dichloromethane and mixtures of solvents. When the spray drying solution comprises an organic solvent that is water miscible, such as acetone or methanol, water may be added to the solution. The spray drying solution is then sprayed through an atomizer such as a pressure nozzle or two fluid nozzle into a spray drying chamber. The droplets are contacted with a heated drying gas such as dry nitrogen. Droplets dry rapidly, forming particles of the solid amorphous dispersion comprising the active agent and cationic dextran polymer derivatives. The particles exit the spray dryer and are collected, such as in a cyclone. Subsequent processes may be used to remove any residual solvent from the particles.

In one embodiment, a method includes administering to an animal, including humans, a composition comprising a plurality of particles, the particles comprising an active agent and a cationic dextran polymer derivative, via a mode selected from oral, buccal, mucosal, sublingual, intravenous, intra-arterial, intramuscular, subcutaneous, intraperitoneal, intraarticular, infusion, intrathecal, intraurethral, topical, subdermal, transdermal, intranasal, inhalation, pulmonary tract, intratracheal, intraocular, ocular, intraaural, vaginal, and rectal.

In one embodiment, a method of treating a subject, such as animals, including humans, in need of therapy comprises administering a composition comprising an active agent and a cationic dextran polymer derivative to an animal via a mode selected from oral, buccal, mucosal, sublingual, intravenous, intra-arterial, intramuscular, subcutaneous, intraperitoneal, intraarticular, infusion, intrathecal, intraurethral, topical, subdermal, transdermal, intranasal, inhalation, pulmonary tract, intratracheal, intraocular, ocular, intraaural, vaginal, and rectal.

In one embodiment, the compositions comprising the active agent and cationic dextran polymer derivatives are intended for inhalation. As used herein, the term "inhalation" refers to delivery to a subject through the mouth and/or nose. In one embodiment, the dry powder suitable for inhalation is delivered to the "upper airways." The term "upper airways" refers to delivery to nasal, oral, pharyngeal, and/or laryngeal passages, including the nose, mouth, nasopharynx, oropharynx, and/or larynx. In another embodiment, the dry powder suitable for inhalation is delivered to the "lower airways." The term "lower airways" refers to delivery to the trachea, bronchi, bronchioles, alveolar ducts, alveolar sacs, and/or alveoli.

In one embodiment, the particles have a mass median aerodynamic diameter (MMAD) of 0.5 to 100 µm. In another embodiment, the particles have a MMAD of 10 to 70 µm. In yet another embodiment, the particles have an average diameter of 50 µm. In one embodiment, such particles are used in devices designed for delivery of particles to the upper airways. In another embodiment, such particles are used in devices designed for delivery of particles via the nose.

In one embodiment, the particles are intended for inhalation and have a MMAD of 0.5 to 100 µm. In another embodiment, the particles are intended for inhalation and have a MMAD of 0.5 to 70 µm.

In one embodiment, the particles are intended for delivery to the upper airways, and have a MMAD of greater than 10 µm. In another embodiment, the particles are intended for delivery to the upper airways and have a MMAD of 10 to 100 µm, and wherein the weight fraction of particles having an aerodynamic diameter of less than 10 µm is less than 0.1. In another embodiment, the particles are intended for delivery to the upper airways and have a MMAD of 10 to 70 µm, and the weight fraction of particles having an aerodynamic diameter of less than 10 µm is less than 0.1.

In another embodiment, the particles are intended for delivery to the lower airways, and have a MMAD of less than 10 µm. In one embodiment, the particles are intended for delivery to the lower airways, and have a MMAD of 0.5 to 10 µm, and the weight fraction of particles having an aerodynamic diameter of greater than 10 µm is less than 0.1. In another embodiment, the particles are intended for delivery to the lower airways, and have a MMAD of 0.5 to 7 µm, and the weight fraction of particles having an aerodynamic diameter of greater than 7 µm is less than 0.1.

In one embodiment, the compositions may be formulated as a dry powder for use in a suitable inhalation device, such as a conventional dry powder inhaler. In another embodiment, the powders may be packaged in a packet suitable for insertion into a dry powder inhaler. Suitable dry powder inhalers typically rely on a burst of inspired air that is drawn through the unit to deliver the powder to the desired location. In another embodiment, the compositions may be administered as aqueous solutions or suspensions, or as solutions or suspensions in propellants, using, for example, a metered-dose inhaler. In this embodiment, the solution or suspension is aerosolized by liquid nebulizers employing either hydraulic or ultrasonic atomization. Compressor-driven nebulizers may also be employed, which may use a suitable propellant.

Other features and embodiments of the disclosure will become apparent from the following Examples that are given for illustrating certain embodiments of the disclosure rather than for limiting the intended scope.

EXAMPLES

Polymer 1, dextran propionate quaternary amine having the structure and degree of substitution shown in Table 1, was synthesized using the following procedure. First, 3.53 g (3-carboxypropyl)trimethyl ammonium chloride was dissolved in 30 mL of a solvent consisting of 1:2 (vol:vol) dimethyl formamide (DMF)/formamide. To this solution was added 3.52 g 1,1-carbonyldiimidazole with rapid stirring. Next, a second solution was formed by dissolving 10.01 g dextran (that had been dried for 24 hours at 90° C.) in 50 mL formamide at 50° C. The dextran had an average molecular weight of 40,000 daltons (obtained from Amersham Biosciences, Piscataway, N.J.). After the first solution had stirred for 3.5 hours, the two solutions were combined and stirred 18.5 hours at 50° C. in a sealed round bottom flask equipped with a condenser.

To form the dextran propionate quaternary amine, 8.89 g sodium propionate and 50 mL formamide was added to the reaction mixture, and the mixture stirred at 50° C. for about an hour. To this, 23.06 g propionic anhydride was added, and stirring continued at 50° C. for about 2 hours before an additional 9.41 g propionic anhydride was added. Stirring continued at 50° C. for 18 hours following addition of the second aliquot of propionic anhydride.

Approximately half of the reaction mixture was poured into 800 mL water, and sodium chloride was added until the solution became cloudy. The cloudy gelatinous mixture was centrifuged to isolate the solid polymer. The solid polymer was collected and added to 600 mL water, and the slurry was centrifuged to isolate solid product. This water wash process was repeated. The solid product was dissolved in 350 mL methanol. To this, 400 mL isopropyl alcohol (IPA) was added and the solvent was removed using rotary evaporation under vacuum (rotoevaporated). An additional 200 mL IPA was added, followed by solvent removal. The solid polymer was dried under vacuum for 48 hours. For a final purification step, the polymer was dissolved in methylene chloride, filtered through a 0.2 μm filter, and rotoevaporated. The solid polymer was dried in a vacuum desiccator.

Figure 1:
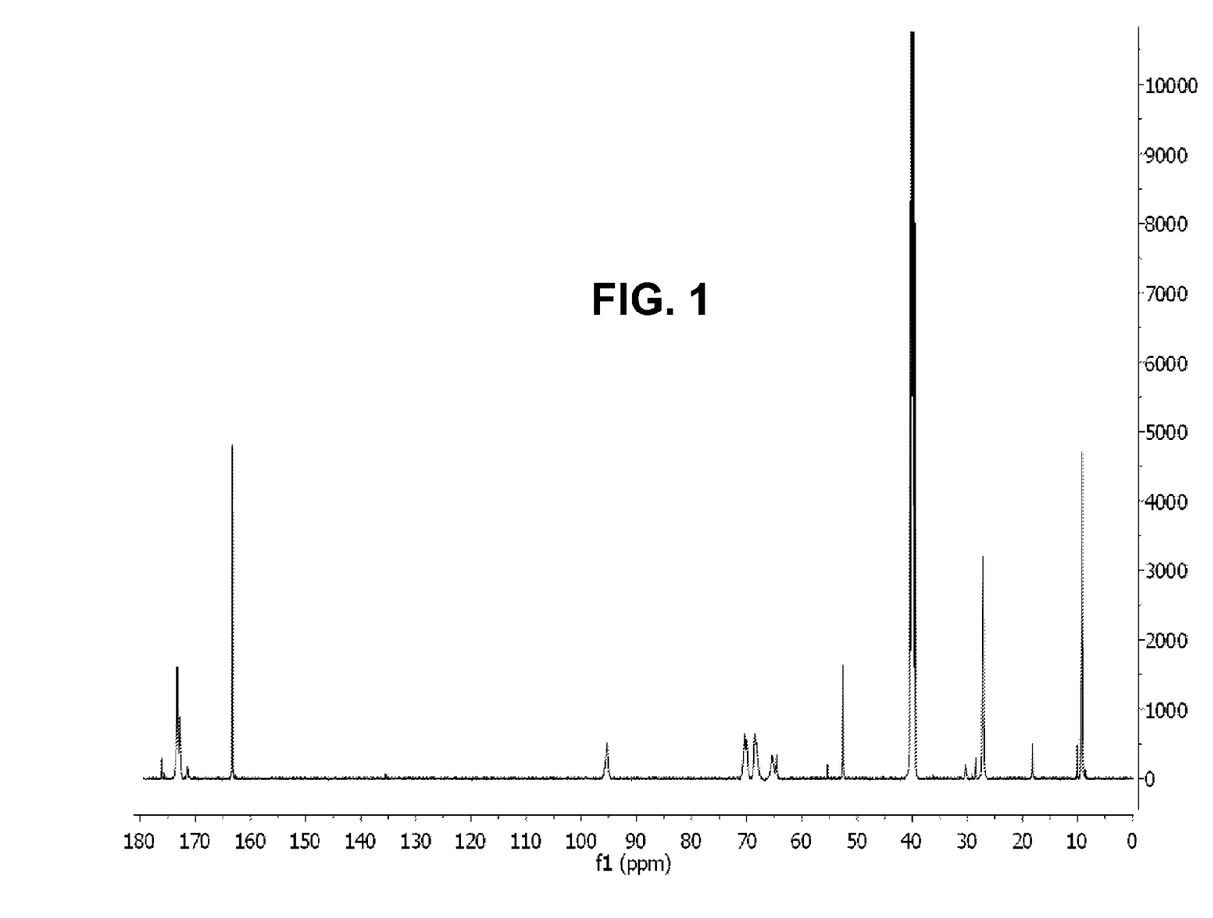
FIG. 1 shows the $^{13}$C nuclear magnetic resonance (NMR) spectrum of Polymer 1.

The polymer was analyzed by $^{13}$C nuclear magnetic resonance (NMR) spectroscopy to examine propionate and quaternary amine substitutions on the dextran backbone (see FIG. 1). For NMR analysis, polymer samples were dissolved in deuterated dimethyl sulfoxide (DMSO) at a concentration of 200 mg/mL. Propionate and quaternary amine group concentrations were determined using the ratios of peak areas to the peak area of the anomeric carbon in the dextran ring. Polymer properties are shown in Table 1.

TABLE 1

| Polymer | Starting Dextran/ Molecular Weight (Daltons) | Alkyl Ester Substituent | Degree of Substitution of the Alkyl Ester Substituent | Ester-Linked Amine-Containing Substituent | Degree of Substitution of the Amine-Containing Substituent |
|---|---|---|---|---|---|
| 1 | Dextran 40,000 | propionate | 2.8 | ester-linked trimethylammonium | 0.22 |
| 2 | Dextran 40,000 | acetate | 1.0 | ester-linked trimethylammonium | 0.14 |
| 3 | Dextran 20,000 | acetate | 1.9 | ester-linked trimethylammonium | 0.14 |
| 4 | Dextran 10,000 | propionate | 1.9 | ester-linked trimethylammonium | 0.04 |
| 5 | Dextran 20,000 | propionate | ND* | ester-linked β-alanine (NH$_2$) | ND |

* ND = not determined

Polymer 2, dextran acetate quaternary amine having the structure and degree of substitution shown in Table 1, was synthesized using the following procedure. First, dextran quaternary amine was synthesized by dissolving 3.005 g (3-carboxypropyl)trimethylammonium chloride in 30 mL DMF/formamide (1:2 vol:vol). To this, 3.004 g 1,1-carbonyldiimidazole was added in small portions (200-300 mg) with rapid stirring. After foaming ceased, the solution was stirred for 2 hours at room temperature. Next, a second solution was formed by dissolving 9.023 g dextran having an average molecular weight of 40,000 daltons (Amersham Biosciences; dried at least 24 hours at 90° C.) in 50 mL formamide at 50° C. The two solutions were combined and stirred for about 18 hours at 50° C. in a sealed round bottom flask equipped with a condenser.

To form the dextran acetate quaternary amine, 8.779 g sodium acetate was added to the reaction mixture, followed by 7.144 g acetic anhydride. The reaction mixture was stirred at 50° C. for 5 hours. The reaction mixture was removed from the heat and stirred about 18 hours at room temperature.

Figure 2:
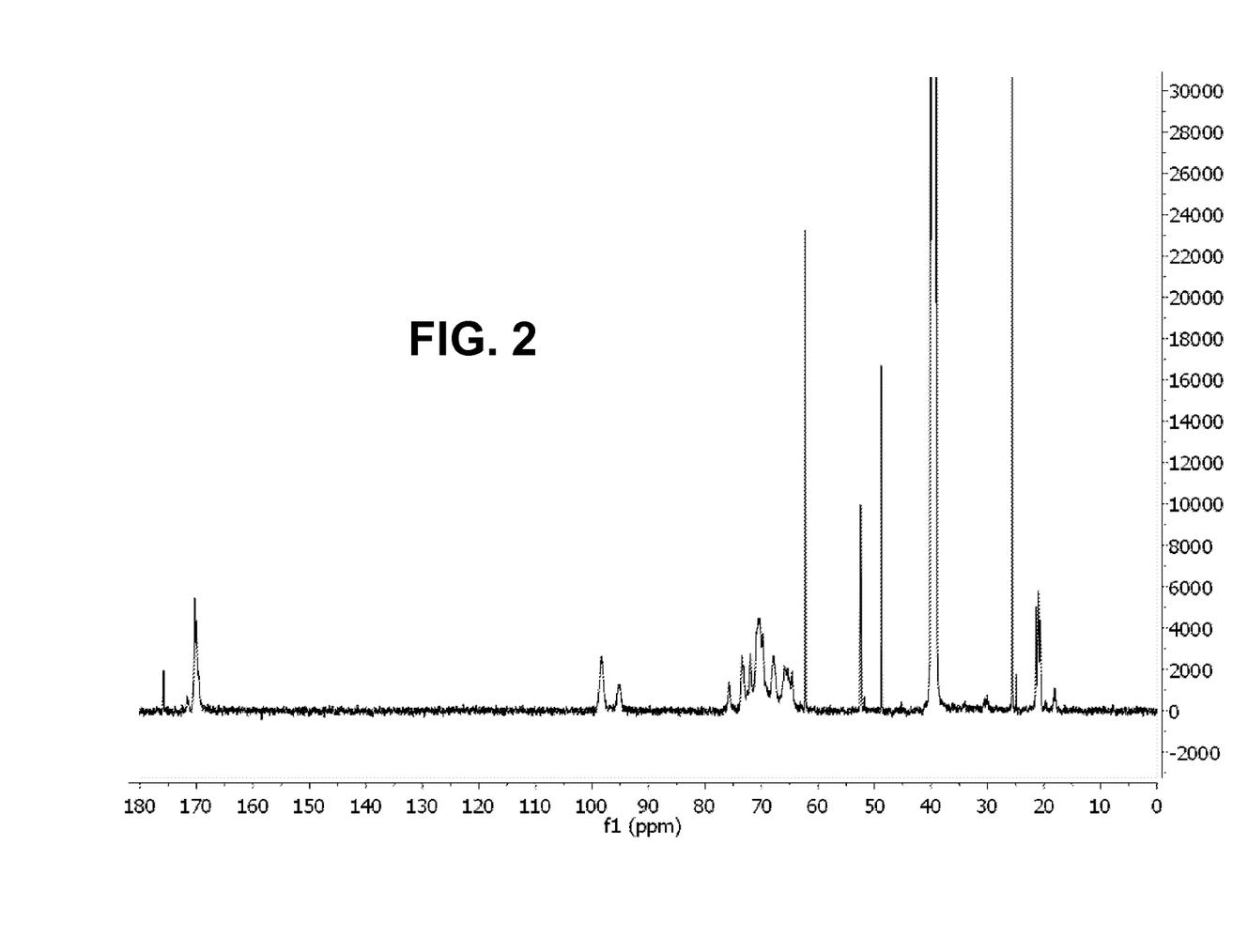
FIG. 2 shows the $^{13}$C nuclear magnetic resonance (NMR) spectrum of Polymer 2.

Approximately one third of the reaction mixture was poured into 800 mL acetone to precipitate the polymer and remove organic solvent. The solid polymer material was collected by filtration (Whatman 113 filter paper, Piscataway, N.J.), added to 400 mL acetone, and filtered again. The filtrate material was rinsed with 200 mL acetone and dried under vacuum. For a final purification step, the polymer was dissolved in 150 mL water and the pH was adjusted to about 5 using 6N HCl. The polymer solution was poured into a dialysis membrane tube (6000 to 8000 Dalton molecular weight cut off dialysis membrane) and dialyzed for about 2 days using deionized water. Fresh water was added (3.5 L) and dialysis continued for an additional day. After dialysis, IPA was added to the polymer solution (3:1), and the solution was rotoevaporated to dryness. The solid polymer was dried under vacuum. The $^{13}$C NMR spectrum of Polymer 2 is shown in FIG. 2.

Polymer 3, dextran acetate quaternary amine having the structure and degree of substitution shown in Table 1, was synthesized using the following procedure. First, Texas Red dye was attached to dextran for polymer detection. To attach the dye, 6.145 g of dextran having an average molecular weight of 20,000 daltons (Amersham Biosciences; dried 3 days at 90° C.) was dissolved in 50 mL formamide at 50° C., and 1.495 g diisopropylethylamine was added to the reaction mixture. Next, 35 mg of Texas Red dichlorotriazine (available from Invitrogen Corp., Carlsbad, Calif.) was added and rinsed into the dextran solution using anhydrous DMF (20 mL total). The reaction mixture was stirred overnight at 50° C.

Dextran quaternary amine was synthesized by dissolving 1.350 g (3-carboxypropyl)trimethylammonium chloride and 1.479 g 1,1-carbonyldiimidazole in 50 mL DMF/formamide (1:1) at room temperature. This solution was stirred for 2 hours, then added to the dextran-dye reaction mixture above. The reaction was stirred at 50° C. for about 18 hours. The polymer was isolated by precipitation into 900 mL IPA followed by filtration. Next, the polymer was dissolved in 150 mL formamide, precipitated by adding 75 mL of the polymer solution to 900 mL of IPA/ethyl acetate (1:1), and filtered (Whatman 113 filter paper). The product was rinsed with several hundred mL IPA and finally about 200 mL diethyl ether. The solid polymer was dried under vacuum.

To form the dextran-dye acetate quaternary amine, 4.146 g dextran-dye quaternary amine was dissolved in 50 mL formamide at 50° C., and 5.124 g sodium acetate was added to the reaction mixture, followed by 7.073 g acetic anhydride. The reaction mixture was stirred at 50° C. for about 18 hours.

Figure 3:
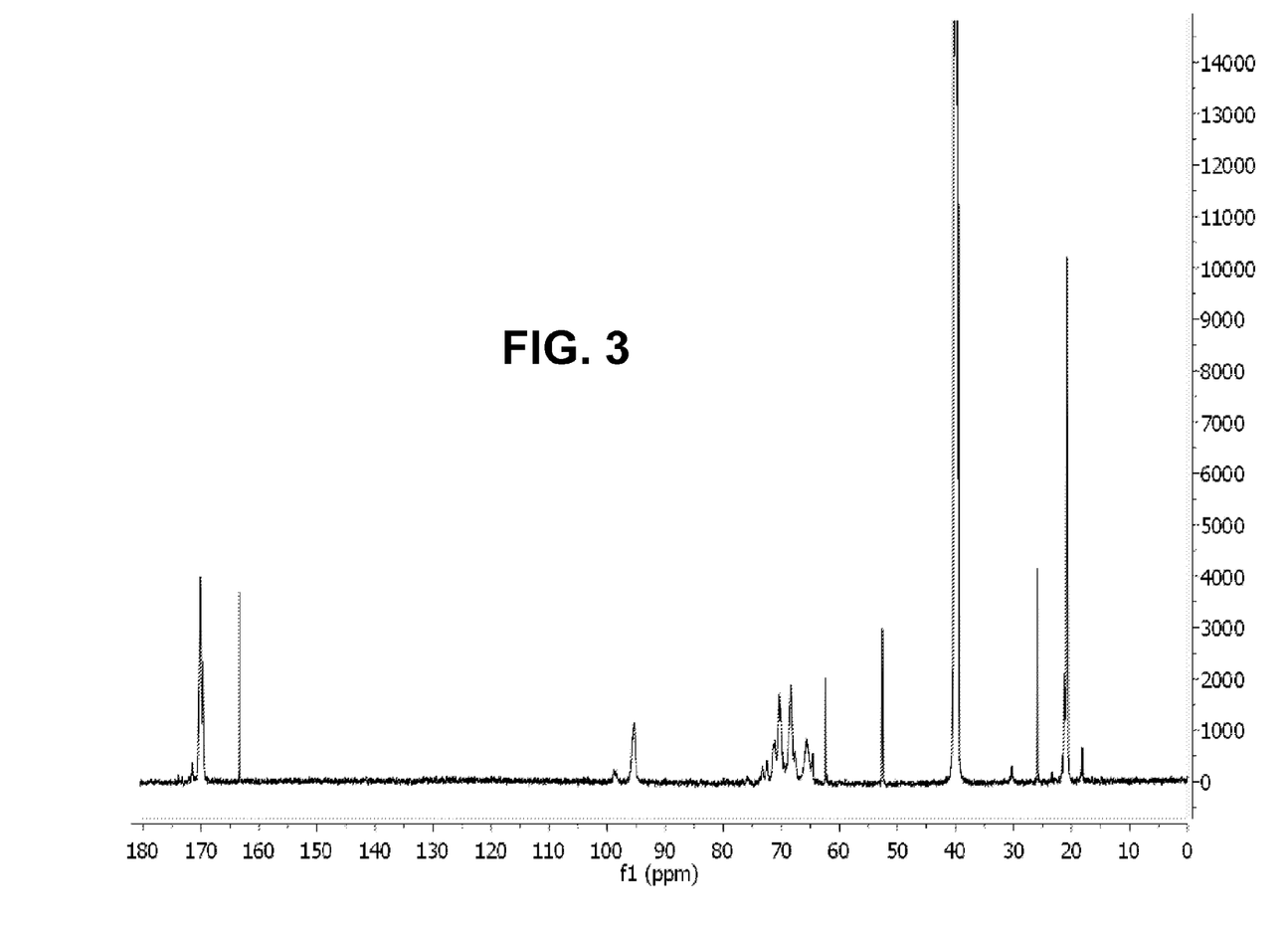
FIG. 3 shows the $^{13}$C nuclear magnetic resonance (NMR) spectrum of Polymer 3.

The reaction mixture was quenched in 400 mL rapidly-stirred water saturated with sodium chloride, forming a gelatinous precipitate. The gelatinous mixture was centrifuged to isolate the solid polymer. The solid polymer was collected and added to 300 mL water, and the slurry was centrifuged to isolate solid product. This water wash process was repeated. The solid product was dissolved in 150 mL methanol, and filtered using a 20 µm filter. To this, 100 mL IPA was added and the solution was rotoevaporated to dryness. The solid polymer was dried under vacuum. The $^{13}$C NMR spectrum of Polymer 3 is shown in FIG. 3.

Polymer 4, dextran propionate quaternary amine having the structure and degree of substitution shown in Table 1, was synthesized using the following procedure. First, dextran propionate was made by dissolving 30.057 g dextran having an average molecular weight of 10,000 daltons (obtained from Amersham) in 100 mL formamide at 50° C. To this, 10.778 g sodium propionate and 65.141 g propionic anhydride was added, and stirring continued at 50° C. for about 18 hours. The resulting dextran propionate was precipitated into 800 mL water in a blender and filtered three times (Whatman 113 filter paper), and the filtrate was washed with an additional 500 mL water. This material was air-dried overnight.

Dextran propionate quaternary amine was synthesized by dissolving 0.661 g (3-carboxypropyl)trimethylammonium chloride and 0.665 g 1,1-carbonyldiimidazole in 50 mL formamide. The solution was stirred for 6.5 hours. To this, 4.015 g dextran propionate (above) was added, and the reaction mixture was stirred for about 16 hours.

Figure 4:
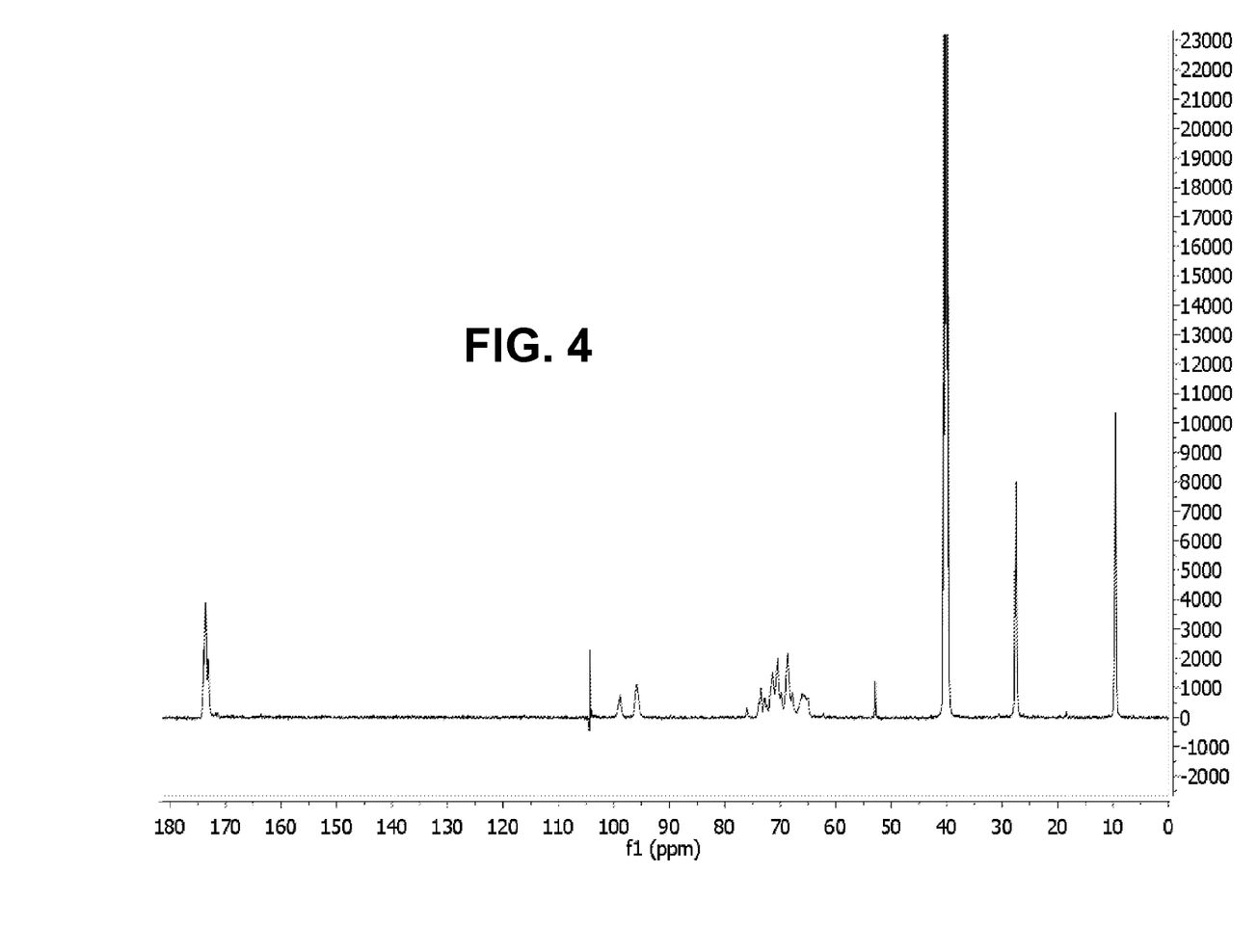
FIG. 4 shows the $^{13}$C nuclear magnetic resonance (NMR) spectrum of Polymer 4.

The reaction mixture was poured into 800 mL water, and sodium chloride was added until the material flocculated. The material was filtered using a 0.45 µm filter to isolate the solid polymer. The material was dissolved in methanol, and filtered (Whatman 113 filter paper). The solution was rotoevaporated to dryness. The polymer was dried under vacuum for 3 hours, dissolved in 80 mL methanol, and precipitated into 400 mL water with stirring. The polymer suspension was poured into a dialysis membrane tube (6000 to 8000 Dalton molecular weight cut off dialysis membrane) and dialyzed using deionized water. Following dialysis, the suspension was mixed with IPA (7:3 IPA/polymer suspension), and rotoevaporated to dryness. The solid polymer was dissolved in 50 mL methanol and rotoevaporated to dryness again. The polymer was dried under vacuum. The $^{13}$C NMR spectrum of Polymer 4 is shown in FIG. 4.

Polymer 5 dextran propionate primary amine, having the structure shown in Table 1, was synthesized using the following procedure. First, dextran primary amine was synthesized by dissolving 5.027 g N-(9-Fluorenylmethoxycarbonyl)-beta-alanine (Fmoc-β-alanine) and 2.701 g 1,1-carbonyldiimidazole in 50 mL dimethylformamide (DMF). Next, a second solution was formed by dissolving 7.039 g dextran having an average molecular weight of 20,000 daltons (Amersham Biosciences; dried 2 days at 90° C.) in 50 mL formamide. After the first solution had stirred for several hours, the two solutions were combined and stirred overnight at room temperature in a sealed round bottom flask equipped with a condenser.

To form the dextran propionate primary amine, 9.41 g sodium propionate and 34.62 g propionic anhydride was added to the reaction mixture and heated to about 50° C. until the mixture was clear. The reaction mixture was stirred overnight at room temperature.

To isolate the product, the reaction mixture was poured into 1800 mL water with stirring to precipitate the polymer. The solid polymer material was collected by filtration (Whatman 113 filter paper), and rinsed with 400 mL water. The material was redissolved in 100 mL acetone to form a clear solution. The acetone solution was then poured into 1800 mL water, and sodium chloride was added to precipitate the polymer material. The material was filtered and rinsed with 200 mL water, and dried on filter paper (Whatman 113 filter paper) with the vacuum.

The Fmoc protecting group was removed by adding 6.93 g of dried product to 50 mL DMF. Next, 15 mL piperidine was added, and the mixture was stirred for 45 minutes at room temperature. The solution was poured into 1800 mL water containing 13 mL of 12 N HCl. Sodium chloride was added until saturation was obtained, to precipitate the polymer. The polymer was collected by filtration (Whatman 113 filter paper) and rinsed with water. The polymer was redissolved in methanol, the solution was filtered through a 5 µm filter, and the solvent was removed using rotary evaporation under vacuum. The solid polymer was dissolved again in methanol, filtered, and rotoevaporated to dryness. The material was further purified by adding 1.03 g polymer and 2.1 g piperidine on Rasta Resin (polystyrene crosslinked with divinylbenzene scavenger resin beads, available from Sigma-Aldrich Co.) to 20 mL methanol:methylene chloride 1:1, and stirring overnight at room temperature. The Rasta Resin was removed by filtration (20 µm nylon filter), and the solvent was rotoevaporated to dryness. A ninhydrin test on the polymer spotted on silica confirmed the presence of the primary amine functional group.

Composition 1

A composition may be formed using Polymer 1 and the active agent 3,5-dimethyl 2,6-dimethyl-4-(2-nitrophenyl)-1,4-dihydropyridine-3,5-dicarboxylate, also known as nifedipine, having the structure:

Nifedipine has a water solubility of 10 μg/mL and a C Log P value of 3.1.

A spray solution may be formed by dissolving 0.2 wt % nifedipine and 1.8 wt % Polymer 1 in methylene chloride or other suitable solvent. The resulting solution may then be spray dried by atomizing the solution using a two-fluid nozzle into a spray drying chamber to form droplets of the spray solution. The droplets may be mixed with nitrogen drying gas at 100° C. in a drying chamber, forming a solid powder having an average particle size ranging from 5 to 30 μm in diameter.

Composition 2

A composition may be formed using Polymer 5 and nifedipine by dissolving 0.2 wt % nifedipine and 1.8 wt % Polymer 5 in a suitable solvent. The resulting solution may then be spray dried by atomizing the solution using a pressure nozzle into a spray drying chamber to form droplets of the spray solution. The droplets may be mixed with nitrogen drying gas at 120° C. in a drying chamber, forming a solid powder having an average particle size ranging from 5 to 30 μm in diameter.

In one embodiment, a solid dry powder composition comprises (a) an active agent; and (b) a dextran polymer derivative comprising (i) an ester-linked amine-containing substituent, selected from and mixtures thereof, wherein $R_1$ is selected from $C_1$, $C_2$, $C_3$, or $C_4$ alkyl groups, $R_2$ and $R_3$ may be the same or different and are selected from hydrogen, methyl and ethyl groups, and $R_4$, $R_5$, and $R_6$ may be the same or different and are selected from methyl and ethyl groups, and wherein the degree of substitution of said ester-linked amine-containing substituent is at least 0.03, and (ii) an alkyl ester substituent selected from acetate, propionate, butyrate, isobutyrate, and mixtures thereof, wherein the degree of substitution of said alkyl ester substituent is at least 0.05.

In some embodiments, the ester-linked amine-containing substituent is wherein $R_1$ is selected from $C_1$, $C_2$, $C_3$, or $C_4$ alkyl groups, and $R_2$ and $R_3$ may be the same or different and are selected from hydrogen, methyl and ethyl groups. In certain embodiments, $R_1$ is a $C_2$ alkyl group, and $R_2$ and $R_3$ are hydrogens.

In some embodiments, the ester-linked amine-containing substituent is wherein $R_1$ is selected from $C_1$, $C_2$, $C_3$, or $C_4$ alkyl groups, and $R_4$, $R_5$, and $R_6$ may be the same or different and are selected from methyl and ethyl groups. In certain embodiments, $R_1$ is a $C_3$ alkyl group, and $R_4$, $R_5$, and $R_6$ are methyl groups.

In any or all of the above embodiments, the ester-linked amine-containing substituent may have a degree of substitution of at least 0.05. In some embodiments, the ester-linked amine-containing substituent has a degree of substitution of at least 0:1.

In any or all of the above embodiments, the degree of substitution of the alkyl ester substituent may be at least 0.1. In any or all of the above embodiments, the degree of substitution of the alkyl ester substituent may be at least 0.5. In any or all of the above embodiments, the degree of substitution of the alkyl ester substituent may be at least 1.0.

In any or all of the above embodiments, the alkyl ester substituent may be selected from acetate and propionate. In any or all of the above embodiments where $R_1$ is a $C_2$ alkyl group, and $R_2$ and $R_3$ are hydrogens, the alkyl ester substituent may be propionate. In any or all of the above embodiments where $R_1$ is a $C_3$ alkyl group, and $R_4$, $R_5$, and $R_6$ are methyl groups, the alkyl ester substituent may be acetate. In any or all of the above embodiments where $R_1$ is a $C_3$ alkyl group, and $R_4$, $R_5$, and $R_6$ are methyl groups, the alkyl ester substituent may be propionate.

In any or all of the above embodiments, the composition may be formulated for administration to a human or animal via a mode selected from oral, buccal, mucosal, sublingual, intravenous, intra-arterial, intramuscular, subcutaneous, intraperitoneal, intraarticular, infusion, intrathecal, intraurethral, topical, subdermal, transdermal, intranasal, inhalation, pulmonary tract, intratracheal, intraocular, ocular, intraaural, vaginal, and rectal. In some embodiments, the composition is formulated for administration to a human or animal via inhalation. In one embodiment, the composition is formulated for delivery to the upper airways. In another embodiment, the composition is formulated for delivery to the lower airways.

In any or all of the above embodiments, the active agent may be selected from a small molecule, a biological active agent, and mixtures thereof. In some embodiments, the active agent is a biological active agent selected from proteins, antibodies, antibody fragments, antigens, peptides, oligonucleotides, vaccines, and mixtures and derivatives thereof. In certain embodiments, the composition is formulated for delivery to the nasal passages.

A method comprises providing a solid dry powder composition according to any or all of the above embodiments, wherein the composition is formulated for inhalation by a human or animal. In any or all embodiments, the composition may be formulated for delivery to the upper airways. In any or all embodiments, the composition may be formulated for delivery to the lower airways. In any or all embodiments, the composition may be formulated for delivery to the nasal passages.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A solid dry powder composition comprising:
   (a) an active agent; and
   (b) a dextran polymer comprising
      (i) an ester-linked amine-containing substituent, selected from and mixtures thereof, wherein $R_1$ is selected from $C_1$, $C_2$, $C_3$, or $C_4$ alkyl groups, $R_2$ and $R_3$ may be the same or different and are selected from hydrogen, methyl and ethyl groups, and $R_4$, $R_5$, and $R_6$ may be the same or different and are selected from methyl and ethyl groups, and wherein the degree of substitution of said ester-linked amine-containing substituent is at least 0.03, and
      (ii) an alkyl ester substituent selected from acetate, propionate, butyrate, isobutyrate, and mixtures thereof, wherein the degree of substitution of said alkyl ester substituent is at least 0.05.

2. The composition of claim 1 wherein said ester-linked amine-containing substituent is wherein $R_1$ is selected from $C_1$, $C_2$, $C_3$, or $C_4$ alkyl groups, and $R_2$ and $R_3$ may be the same or different and are selected from hydrogen, methyl and ethyl groups.

3. The composition of claim 2 wherein $R_1$ is a $C_2$ alkyl group, and $R_2$ and $R_3$ are hydrogens.

4. The composition of claim 3 wherein said alkyl ester substituent is propionate.

5. The composition of claim 1 wherein said ester-linked amine-containing substituent is wherein $R_1$ is selected from $C_1$, $C_2$, $C_3$, or $C_4$ alkyl groups, and $R_4$, $R_5$, and $R_6$ may be the same or different and are selected from methyl and ethyl groups.

6. The composition of claim 5 wherein $R_1$ is a $C_3$ alkyl group, and $R_4$, $R_5$, and $R_6$ are methyl groups.

7. The composition of claim 6 wherein said alkyl ester substituent is selected from acetate and propionate.

8. The composition of claim 1 wherein said ester-linked amine-containing substituent has a degree of substitution of at least 0.05.

9. The composition of claim 1 wherein said degree of substitution of said alkyl ester substituent is at least 0.1.

10. The composition of claim 1 wherein said composition is formulated for administration to a human or animal via a mode selected from oral, buccal, mucosal, sublingual, intravenous, intra-arterial, intramuscular, subcutaneous, intraperitoneal, intraarticular, infusion, intrathecal, intraurethral, topical, subdermal, transdermal, intranasal, inhalation, pulmonary tract, intratracheal, intraocular, ocular, intraaural, vaginal, and rectal.

11. The composition of claim 10 wherein said composition is formulated for administration to a human or animal via inhalation.

12. The composition of claim 11 wherein said composition is formulated for delivery to the upper airways.

13. The composition of claim 11 wherein said composition is formulated for delivery to the lower airways.

14. The composition of claim 1 wherein said active agent is selected from a small molecule having a molecular weight of 2000 Daltons or less, a biological active agent, and mixtures thereof.

15. The composition of claim 14 wherein said active agent is a biological active agent selected from proteins, antibodies, antibody fragments, antigens, peptides, oligonucleotides, vaccines, and mixtures thereof.

16. The composition of claim 15 wherein said composition is formulated for delivery to the nasal passages.

17. A method, comprising:
   providing a solid dry powder composition formulated for inhalation by a human or animal, the solid dry powder composition comprising an active agent and a dextran polymer comprising
      (i) an ester-linked amine-containing substituent, selected from and mixtures thereof, wherein $R_1$ is selected from $C_1$, $C_2$, $C_3$, or $C_4$ alkyl groups, $R_2$ and $R_3$ may be the same or different and are selected from hydrogen, methyl and ethyl groups, and $R_4$, $R_5$, and $R_6$ may be the same or different and are selected from methyl and ethyl groups, and wherein the degree of substitution of said ester-linked amine-containing substituent is at least 0.03, and
      (ii) an alkyl ester substituent selected from acetate, propionate, butyrate, isobutyrate, and mixtures thereof, wherein the degree of substitution of said alkyl ester substituent is at least 0.05.

18. The method of claim 17 wherein said composition is formulated for delivery to the upper airways.

19. The method of claim 17 wherein said composition is formulated for delivery to the lower airways.

20. The method of claim 17 wherein said composition is formulated for delivery to the nasal passages.

* * * * *